United States Patent
Zimmermann et al.

(10) Patent No.: US 9,781,918 B2
(45) Date of Patent: Oct. 10, 2017

(54) SUBSTRATE UNIT, PRESERVATION DEVICE AND METHOD FOR THE CRYOPRESERVATION OF A BIOLOGICAL SAMPLE

(71) Applicant: Fraunhofer-Gesellschaft zur Foerderung der angewandten Forschung e.V., Munich (DE)

(72) Inventors: Heiko Zimmermann, Waldbrunn (DE); Axel Beier, Vogt (DE); Julia Neubauer, St. Ingbert (DE); Guenter R. Fuhr, Berlin (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 167 days.

(21) Appl. No.: 14/412,615

(22) PCT Filed: Jul. 1, 2013

(86) PCT No.: PCT/EP2013/001920
§ 371 (c)(1),
(2) Date: Jan. 2, 2015

(87) PCT Pub. No.: WO2014/005690
PCT Pub. Date: Jan. 9, 2014

(65) Prior Publication Data
US 2015/0125954 A1    May 7, 2015

(30) Foreign Application Priority Data
Jul. 4, 2012 (DE) .......................... 10 2012 013 267

(51) Int. Cl.
*A01N 1/02* (2006.01)
*C12M 1/00* (2006.01)

(52) U.S. Cl.
CPC .............. *A01N 1/021* (2013.01); *C12M 45/22* (2013.01)

(58) Field of Classification Search
CPC ...................................................... C12M 45/22
(Continued)

(56) References Cited

U.S. PATENT DOCUMENTS 3,499,825 A    3/1970    Falcone et al.
5,257,128 A    10/1993   Diller et al.
(Continued)

FOREIGN PATENT DOCUMENTS

DE    8908583.3 U1    9/1993
DE    19827875 A1    12/1999
(Continued)

OTHER PUBLICATIONS

English language abstract for JP 2012-034667 A (2012).
(Continued)

*Primary Examiner* — Michael Hobbs
(74) *Attorney, Agent, or Firm* — Caesar Rivise, PC

(57) ABSTRACT

A substrate unit for cryopreservation of a biological sample includes: a substrate platform having on a front side thereof a cultivation surface for receiving the biological sample; a first chamber including the cultivation surface of the substrate platform, wherein the first chamber is configured for receiving a cultivation liquid; a second chamber configured for receiving a temperature control medium; and a chamber bracket for receiving the substrate unit in a cryopreservation device in a pivotable manner, wherein the first and second chambers are connected to each other in an adjacent manner, and the substrate platform forms a separating wall between the first chamber and the second chamber, and wherein the back side of the substrate platform faces the second chamber. The invention further relates to a cryopreservation
(Continued)

device, wherein the substrate unit is arranged in a rotatable manner, and a method for the cryopreservation of a biological sample.

19 Claims, 10 Drawing Sheets

(58) Field of Classification Search
USPC .................................................. 435/307.1
See application file for complete search history.

(56) References Cited

U.S. PATENT DOCUMENTS

| | | | |
|---|---|---|---|
| 5,650,325 | A | 7/1997 | Spielmann |
| 5,964,096 | A | 10/1999 | Watson et al. |
| 2004/0214313 | A1* | 10/2004 | Zhang .................... C12M 23/10 435/288.4 |
| 2006/0154232 | A1 | 7/2006 | Degel et al. |
| 2010/0062529 | A1 | 3/2010 | Zimmermann et al. |
| 2013/0267019 | A1* | 10/2013 | Schmidt ................ C12M 23/12 435/297.1 |
| 2014/0335555 | A1* | 11/2014 | Kim ..................... A01N 1/0242 435/29 |

FOREIGN PATENT DOCUMENTS

| | | |
|---|---|---|
| DE | 69633854 T2 | 10/2005 |
| DE | 2434873 A2 | 4/2012 |
| EP | 2434873 A2 | 4/2012 |
| GB | 1539263 | 1/1979 |
| JP | 2012034667 A | 2/2012 |
| WO | 9640858 A1 | 12/1996 |
| WO | 9908513 A1 | 2/1999 |
| WO | 2010136118 A2 | 12/2010 |
| WO | 2012024408 A2 | 2/2012 |
| WO | 2012024408 A3 | 2/2012 |

OTHER PUBLICATIONS

English-language abstract for DE19827875A1, dated Oct. 13, 2014.
Beier et al., "Effective surface-based cryopreservation of human embryonic stem cells by vitrification", Cryobiology, vol. 63, pp. 175-185 (2011).
Heng et al. "The cryopreservation of human embryonic stem cells", in "Biotechnol. Appl. Biochem.", vol. 41, 2005, pp. 97-104.
Kuwayama, "Highly efficient vitrification for cryopreservation of human oocytes and embryos: The Cryotop method", Theriogenology, vol. 67 (2007) pp. 73-80.
Kuwayama et al., "Highly efficient vitrification method for cryopreservation of human oocytes." Reprod Biomed Online 2005; 11(5); pp. 608-614.
Lane et al., "Vitrification of mouse and human blastocysts using a novel cryoloop container-less technique", "Fertil. Steril.", vol. 72, 1999, pp. 1073-1078.
Richards et al., "An efficient and safe xeno-free cryopreservation method for the storage of human embryonic stem cells." Stem Cells, vol. 22, 2004, pp. 779-789.
Sansinema et al. "Numerical simulation of cooling rates in vitrification systems used for oocyte cryopreservation." "Cryobiology", vol. 63, 2011, pp. 32-37.
Stoop et al., "Clinical validation of a closed vitrification system in an oocyte-donation programme." Reprod Biomed Online; Feb. 2012;24(2):180-5 (Abstract Only).
Vajta et al., "Open pulled straw vitrification: a new way to reduce cryoinjuries of bovine ova and embryos." Mol Reprod Dev vol. 51, 1998, pp. 53-58.
International Search Report for PCT/EP2013/001920 (dated Sep. 6, 2013).

\* cited by examiner

A

B

C

SUBSTRATE UNIT, PRESERVATION DEVICE AND METHOD FOR THE CRYOPRESERVATION OF A BIOLOGICAL SAMPLE

BACKGROUND OF THE INVENTION

The invention relates to a substrate device which is configured for the cryopreservation of a biological sample containing biological cells, and which comprises in particular a cultivation surface for receiving the biological sample and a chamber for receiving the cultivation surface and a cultivation liquid. The invention further relates to a cryopreservation apparatus provided with at least one such substrate device. The invention further relates to a method for the cryopreservation of a biological sample containing biological cells which is carried out with said substrate device or the cryopreservation apparatus. The invention is used for the cryopreservation of biological cells, in particular for the cryopreservation of stem cells, e.g. human embryonic stem cells, or of germ cells, e.g. oocytes.

It is known that, for long-term storage, human embryonic stem cells (hESC) are subjected to cryopreservation (storage in the frozen state). One designated method, for example, is "slow rate freezing", where tried-and-tested cryopreservation methods that work with other cell types are adapted for hESC. The cells are detached from a cultivation surface and frozen in suspension in sample vessels at slow cooling rates with the addition of cryoprotective agents (e.g. 10% DMSO). The samples are recovered by thawing e.g. in a waterbath (cf. e.g. B. C. Heng et al. in "Biotechnol. Appl. Biochem." vol. 41, 2005, pp 97-104). The "slow rate freezing" method has disadvantages in terms of a low efficacy and reliability, chemical and mechanical stress when the cells detach from the cultivation surface, a low survival rate of the cells and a limited functionality of the thawed cells. Thus, after thawing, the cells can only grow to a limited extent on cultivation surfaces, requiring long recultivation times.

One known alternative to "slow rate freezing" is cryopreservation by vitrification (almost instant freezing or rapid freezing), where the cells are frozen at extremely fast cooling rates in order to achieve vitrification (at e.g. 130° C.). Cooling rates are assessed e.g. by M. Sansinena et al. in "Cryobiology" vol. 63(1), 2011, p. 32 ("Numerical simulation of cooling rates in vitrification systems used for oocyte cryopreservation"). A general disadvantage of vitrification is that, to avoid the formation of ice crystals, high concentrations of cryoprotective agents are required; however, these often have toxic effects and impair the result of the cryopreservation.

Because of the extremely fast cooling rates, conventional vitrification is restricted to small volumes of samples (cells and cryomedium). It has generally been the case hitherto that the smaller the volume, the larger is the surface-to-volume ratio of the sample, and the smaller the distance between the sample and a cooling medium, the greater is the probability of successful vitrification.

Another general limitation of conventional vitrification derives from the Leidenfrost phenomenon, which is distinguished by the formation of gas bubbles when warm surfaces come into contact with liquid nitrogen. Insulating regions can form which reduce the cooling rate and hence the chance of successful vitrification.

Furthermore, conventional vitrification makes high demands on the materials, which are expected to tolerate large and rapid temperature differences. In the case of vitrification substrates, the cracking or displacement of components can cause cell damage or reduce sample sterility. It is therefore of interest to find suitable materials or methods that prevent material damage and minimize wear.

One known method, for example, is in-straw vitrification, wherein the cells are detached from the cultivation surface and, after incubation in a cryomedium, transferred to an open or closed straw, optionally on the tip of a plastic pin (G. Vajta et al. in "Mol. Reprod. Dev." vol. 51, 1998, pp 53-58; M. Richards et al. in "Stem Cells" vol. 22, 2004, pp 779-789; M. Kuwayama et al. in "Theriogenology" vol. 67, 2007, pp 73-80; and M. Kuwayama et al. in "Reprod. Biomed. Online" vol. 11, 2005, pp 608-614).

Although in-straw vitrification has good survival rates, it is unsuitable for large quantities. A very small sample volume and a maximized surface-to-volume ratio greatly reduce the quantity of cells that can be vitrified at one time. The thickness of the straw is very limited because the surface-to-volume ratio would become unfavorable for successful vitrification if the diameter were too large. Lengthening the straw would maintain the surface-to-volume ratio, but, because of the handling, would lead to very long sample incubation times and hence to cell damage.

Moreover, in-straw vitrification is very expensive and success is highly dependent on the individual expertise of the operator. Disadvantages of this method result in particular from the difficulty of handling the samples, which can give rise to inaccuracies in the adjustment of the incubation time in the highly concentrated, toxic cryoprotective agents and to high cell loss on freezing and thawing. Furthermore, the number of cells capable of being vitrified by these methods is very limited.

Another known vitrification method uses a so-called "cryoloop". With the cryoloop, a droplet of sample containing the cells is held in a plastic ring at the end of a pin and immersed in liquid nitrogen (−196° C.) (M. Lane et al. in "Fertil. Steril." vol. 72, 1999, pp 1073-1078). A disadvantage of this method results from the direct contact between the sample and the nitrogen and the danger of contamination of the cells by impurities in the nitrogen.

Another known vitrification method is adherent vitrification, wherein the cells in the adherent state are vitrified on a cultivation surface (A. F. Beier et al. in "Cryobiology" vol. 63, 2011, pp 175-185). The method proposed by A. F. Beier is illustrated schematically in FIG. 11 (state of the art). Firstly, biological cells 2' are cultivated on a substrate platform 10' in the adherent state, the substrate platform 10' being arranged in a vessel 20' containing a cultivation liquid 3' (FIG. 11A). The cultivation liquid 3' comprises e.g. a nutrient medium and at least one cryoprotective agent. For vitrification of the biological cells 2', the substrate platform 10' is transferred to another vessel 30' containing liquid nitrogen as the cooling medium 4' (FIG. 11B). Vitrification of the cells 2' takes place in the vessel 30'. For permanent storage the substrate platform 10' is placed in the vapor of the liquid nitrogen 4' in a nitrogen tank 60' (FIG. 11C).

This method again has a disadvantage resulting from the direct contact between the sample and the nitrogen and the consequent danger of contamination of the cells by impurities in the nitrogen. In particular, the possibility of clinical use is greatly restricted because of the risk of microbial contaminations (D. Stoop et al. in "Reprod. Biomed. Online" vol. 24, 2012, pp 180-185). Methods of sterilizing liquid nitrogen exist, but they are time-consuming and cost-intensive.

Although liquid nitrogen has a high purity directly after production and in practice is of pharmaceutical quality when sold commercially, contaminations due to microorganisms and other impurities can occur during transport and storage. Contaminations can even be transferred to the vapor phase due to aerosol formation on the surface of the liquid nitrogen, impairing the air quality. Methods of purifying liquid nitrogen by filtration have proved laborious and insufficiently reliable in practice.

There is an interest in vitrification methods that are easy to carry out, in particular with less stringent demands on precise observance of the incubation time in the cryomedium. There is also an interest in automating the cryopreservation so as to make the use of hESC more cost-effective, less labor-intensive and more efficient. Automated biobanks, for example, make it possible to store and use stem cells from a large number of patients or organisms.

For successful cryopreservation it is further desirable that, after vitrification, e.g. in a straw, and thawing, the cells be capable of growing again on a cultivation surface before they are made available e.g. for experiments or therapeutic use. There is an interest in minimizing the time between thawing and use so as to maximize the efficiency of the cryopreservation.

Many conventional cultivation methods do not allow the cells to be isolated or to be cultivated in the adherent state prior to cryopreservation. Hanging-droplet cultivation, which makes high demands on in situ cryopreservation, may be mentioned explicitly here. The possibility of novel cryopreservation techniques being usable with these cultivation techniques would bring great advantages and create scope for novel uses.

U.S. Pat. No. 5,257,128 discloses a cryobench for observing cells during freezing and thawing in a controllable liquid medium and at a controllable temperature ranging from 100° C. to −100° C. However, the cryobench is suitable neither for cultivation purposes nor for sample vitrification. DE 696 33 854 T2 discloses a method and a package for maintaining and storing cultivated tissue equivalents at low temperatures using a vessel consisting of a dish, a support with a membrane on which the tissue equivalent is immobilized, and a cover. Again this vessel is not suitable for cultivation purposes or sample vitrification. Cultivation vessels are described in U.S. Pat. No. 5,650,325, WO 9 640 858 A1 and GB 1 539 263 A, which, however are not designed for cryopreservation purposes.

An objective of the invention is to provide an improved substrate device and an improved method for the cryopreservation of a biological sample containing biological cells, said device and method eliminating or minimizing disadvantages and limitations of conventional techniques for the cryopreservation of biological samples. Another objective of the invention is to provide an improved cryopreservation apparatus provided with at least one substrate device for the cryopreservation of the biological sample. In particular, the invention should make available a cryopreservation technique by which a greater quantity of sample can be preserved at one time, which allows reproducible adjustment of the preservation conditions, which excludes potential sample contaminations and/or which allows vitrification of the biological samples.

These objectives are achieved by a substrate device, a cryopreservation apparatus and a method of the invention.

According to a first aspect of the invention, said objective is achieved by the general technical teaching of providing a substrate device, in particular for the cryopreservation of a biological sample containing biological cells, which comprises a substrate platform with a cultivation surface, and a first chamber which contains the cultivation surface of the substrate platform and is configured for receiving a cultivation liquid. According to the invention, the substrate device is provided with a second chamber which is configured for receiving a temperature control medium (cooling medium or heating medium). According to the invention, the first chamber and the second chamber are coupled together. Both chambers are connected to each other in an adjacent manner so that the substrate platform forms a separating wall between the interior of the first chamber and the interior of the second chamber. The first chamber (or first vessel, cultivation compartment) contains the cultivation surface having an areal, preferably flat extension. The cultivation surface is a surface which is made of a biologically compatible material suitable for receiving an adherent cell culture or a hanging-droplet culture. The second chamber (or second vessel, nitrogen compartment) is delimited from the first chamber by the substrate platform. The biological sample in the first chamber is isolated from the surroundings and in particular from the temperature control medium in the second chamber. An exchange between substances in the liquid or gaseous state is ruled out.

Advantageously, the substrate platform provided according to the invention between the first chamber and the second chamber fulfills several functions simultaneously. Firstly, the areal cultivation surface is provided on a front side of the substrate platform wherein the cultivation surface makes it possible to accommodate the biological sample with an extremely high surface-to-volume ratio. The size of the cultivation surface can be chosen without restrictions, so considerably greater quantities of sample can be subjected to cryopreservation than e.g. in the case of in-straw cryopreservation.

Secondly, the substrate platform is a solid component that extends along the laminar dimension of the cultivation surface. Perpendicular to the cultivation surface, i.e. in the direction of the thickness of the substrate platform, the latter extends an essentially smaller extend, thereby creating a negligible distance between the sample and the temperature control medium in terms of the transfer of heat from the temperature control medium to the biological sample. The substrate platform is in the form of a sheet, film or layer of material whose front side, facing towards the first chamber, provides the cultivation surface and whose opposite, back side, facing towards the second chamber, forms a closure with the second chamber.

Thirdly, the substrate platform ensures the separation of biological sample and temperature control medium, in particular the separation of biological sample and liquid nitrogen. Compared with conventional techniques, this affords novel uses of the substrate device with enhanced reliability, especially medical and biotechnological uses, without having to take special precautions to purify the temperature control medium.

According to a second aspect of the invention, the above-stated objective is achieved by the general technical teaching of providing a method for the cryopreservation of a biological sample wherein, in a first step, biological cells are arranged, in particular cultivated, on a cultivation surface of a substrate platform in a cultivation liquid in a first chamber, and in a second step, the temperature of the substrate platform is lowered and the biological sample is converted to a frozen state by filling a cooling medium into a second chamber, adjacent to the first chamber, the substrate platform forming a separating wall between the first chamber and the second chamber. Preferably, the method is carried out with the substrate device according to the above-mentioned first aspect of the invention. Preferably, by filling the cooling medium into the second chamber, the temperature of the substrate platform carrying the biological sample can be lowered rapidly in such a way as to achieve vitrification of the biological sample.

The method according to the invention can be carried out with different types of biological sample. The term "biological sample" denotes any composition of biological cells and a cultivation liquid. The cultivation liquid forms a liquid film or a liquid droplet around the cells. The biological cells include isolated cells, cell groups or cell colonies, in particular in the adherent or suspended state. The biological sample can comprise cells of one single type (identical cells) or cells of different types, e.g. stem cells and differentiated cells. In an advantageous variant of the invention, it is possible e.g. to subject cells of different types in the adherent state to a common cultivation (co-cultivation) on the cultivation surface before freezing takes place under the effect of the cooling medium. The cultivation liquid (cryomedium) generally comprises at least one nutrient medium and at least one cryoprotective agent, e.g. DMSO, propanediol or ethylene glycol. The cryoprotective agent can comprise in particular a composition of 20% DMSO, 20% ethylene glycol and 300 mM trehalose. It is possible to provide one single cultivation liquid at once or a succession of different cultivation liquids each containing different nutrient media and/or cryoprotective agents.

A particular advantage of the method according to the invention is that problems due to the Leidenfrost phenomenon, which were described above, are minimized with the technique according to the invention. Any gas bubbles eventually formed when the cooling medium is filled into the second chamber rise to the top of the second chamber, thus moving away from the substrate platform. The formation of unwanted regions of thermal insulation is therefore avoided.

According to a third aspect of the invention, the above-stated objective is achieved by the general technical teaching of providing a cryopreservation apparatus which comprises at least one substrate device according to the above-mentioned first aspect of the invention, and a rotating device which is configured for receiving and rotating (pivoting) the at least one substrate device. The substrate device is arranged in the cryopreservation apparatus in a rotatable manner. According to the invention, the substrate device can be rotated (pivoted) by means of the rotating device between different states that differ in terms of the arrangement of the first chamber and the second chamber in the vertical direction, i.e. in terms of the direction of gravity. By means of the rotating device the substrate device can be pivoted between a cultivation state, in which the first chamber is arranged above the second chamber in the vertical direction and the substrate platform forms the floor of the first chamber, and a temperature control state, in which the second chamber is arranged above the first chamber and the substrate platform forms the floor of the second chamber.

According to a preferred use of the invention, the substrate device is configured for vitrification of the biological sample on the cultivation surface. For this purpose the thickness and thermal conductivity of the substrate platform are preferably chosen so that, when the back side of the substrate platform, which is preferably exposed towards the interior of the second chamber, is wetted with a cooling medium at a temperature below the glass transition temperature of the sample, e.g. equal to or below −130° C., in particular with liquid nitrogen, the temperature of the biological sample is instantly brought to the temperature of the cooling medium. The glass transition temperature of the sample is e.g. around −130° C., but can be higher or lower depending on the concentration and the conditions, e.g. pressure. The thickness and thermal conductivity of the substrate platform are chosen in particular so as to achieve a cooling rate above minus 5000°/s, particularly preferably above minus 37,500°/s. Advantageously, this achieves cooling rates of practical interest (cf. above, M. Sansinena et al.).

Advantageously, the thickness of the substrate platform can be chosen by those skilled in the art, in particular according to the desired cooling rate, the lateral extent and the required mechanical stability. For the vitrification of the biological sample, it has proved advantageous if the substrate platform in a preferred variant of the invention has a thickness below 200 µm, particularly preferably below 120 µm, e.g. 100 µm or less. Moreover, the vitrification of the biological sample can advantageously be promoted if the substrate platform is made of glass, plastic, semiconductor material, e.g. silicon, or metal, e.g. copper, gold or silver. In general, biocompatible materials are used which have a high thermal conductivity, e.g. the thermal conductivities of the materials mentioned. A glass or plastic substrate platform has advantages in terms of a high mechanical stability and the availability of biocompatible materials. A substrate platform made of semiconductor material or metal also has advantages in terms of a high stability and in terms of a high thermal conductivity as well. Moreover, the use of metal for the substrate platform, or particularly preferably for the entire substrate device, can be advantageous by virtue of the thermal capacity of metals. Even if the cooling failed, e.g. in a nitrogen tank, the required preservation temperature of the sample could be maintained, at least temporarily, thereby minimizing sample losses.

According to another advantageous variant, the substrate platform can be made of a transparent material. Particularly preferably, the substrate platform can be formed in such a way that the biological sample on the cultivation surface can be subjected to an optical investigation, in particular a microscopic investigation. Advantageously, this allows the sample to be observed during freezing and during cryopreservation.

In another advantageous embodiment of the invention, the substrate device is provided with a substrate holder which is configured for a liquid-tight, detachable connection between the substrate platform and the first and/or second chamber. Advantageously, the substrate holder constitutes an anchoring means for exchangeable substrate platforms. The substrate device can be provided with different cultivation surfaces which can be chosen e.g. as a function of the cell types to be preserved and/or the use of the invention.

In another advantageous variant of the invention, the first and/or second chamber of the substrate device is provided with a compensating section. The compensating section is arranged between the substrate platform and the other parts of the first and/or second chamber and is configured for absorbing temperature-dependent mechanical stresses between the substrate platform and the first chamber. If the substrate platform and the other parts of the first or second chamber are made of different materials, the mechanical stresses which can arise when the substrate device is cooled or heated are compensated by the compensating section. The compensating section is e.g. an expansion joint, which forms a flexible buffer zone between the substrate platform and its holder in the first and/or second chamber.

Alternatively or additionally, the first chamber of the substrate device can be provided with a pressure equalizing valve. The pressure equalizing valve is adapted for equalizing any excess pressure between the first chamber and the surroundings. The excess pressure can occur e.g. when the substrate device is heated to recover the biological sample.

In another variant of the invention, the substrate platform can be an integral component of the first chamber or of the complete substrate device. For example, the substrate device can form a single piece with the first and second chambers and the substrate platform. In this case there are advantages in terms of the mechanical stability and compactness of the substrate device. The latter can be made of plastic by an injection molding process, for example.

The substrate device according to the invention advantageously allows different variants for the delivery of the cultivation liquid and/or a temperature control medium. For example, provision can be made for a manual delivery, wherein the respective media are filled into the first or second chamber with a pouring device. Alternatively, the substrate device can be provided with a delivery device which is configured for delivering the cultivation liquid and/or one of the temperature control media. This variant offers advantages for automated use of the substrate device and for increased reproducibility in the delivery of the media and in the observance of given preservation protocols. Advantageously, the delivery device can comprise e.g. a microfluidic device which is integrated into a wall or a cover of the first chamber or the second chamber. The microfluidic unit comprises e.g. a fluidic chip as known per se from microfluidic system technology, which has conducting and metering elements for media delivery. Alternatively or additionally, the delivery device can comprise at least one media line leading into the interior of the first chamber or second chamber. Like the microfluidic unit, the media line can alternatively be integrated into the substrate platform.

In another advantageous variant of the invention, if the first chamber and the second chamber of the substrate device are detachably connected to each other, there can be further advantages for the adaptation the substrate device to the requirement of a concrete use of the invention and for the handling of the substrate device, e.g. when cleaning and when loading the first chamber with the biological sample. In a first variant, the second chamber can be firmly connected to a chamber frame, which is configured for detachably receiving the first chamber. Advantageously, in this case, the second chamber with the chamber frame serves a dual function, firstly in terms of the temperature control of the biological sample in the first chamber, and secondly in terms of the holding of the first chamber. In another variant, the first chamber and the second chamber can be connected to each other via a screw joint.

The implementation of the invention is not restricted to the coupling of one single first chamber with one single second chamber. Particularly for the preservation of cells of different types, it can be advantageous if the first chamber is subdivided into several sub-chambers, each arranged for receiving a separate sample. The sub-chambers are arranged next to each other and adjacent to the second chamber, the substrate platform forming a common separating wall between the sub-chambers and the second chamber. Advantageously, all the samples in all the sub-chambers can be simultaneously brought to temperature, e.g. frozen or thawed, with the temperature control medium in the second chamber.

In another, particularly preferred embodiment of the invention, the substrate device is provided with a chamber holder, which is configured for receiving the substrate device in a pivotable manner in a support, in particular in the cryopreservation apparatus according to the third aspect of the invention. The chamber holder comprises e.g. two supporting elements arranged in a plane parallel to the extent of the substrate platform, which elements can be coupled with the support, e.g. the cryopreservation apparatus. The supporting elements are e.g. spigots which sit in bearings of the support, or pivot bearings for receiving spigots of the support. Advantageously, the chamber holder allows the substrate device to be pivoted rapidly and reproducibly about its lateral axis between the cultivation state and the preservation state.

Advantageously, the cryopreservation according to the invention can be carried out with different types of cell cultures, the cell cultures differing in terms of the provision of the biological cells on the cultivation surface. A first variant of the method according to the invention affords the cryopreservation of adherent biological cells, i.e. biological cells which are arranged on the cultivation surface in an adherent (sticking) manner. In this case, in a first partial step, the substrate device is placed in a cultivation state, in which the first chamber is arranged above the second chamber and the substrate platform forms the floor of the first chamber. The adherent cell culture on the cultivation surface is covered with the cultivation liquid. The biological cells are subjected on the cultivation surface to cultivation, i.e. to cell growth and optionally to cell proliferation under the action of nutrient media and/or differentiation factors in the cultivation liquid. In a further partial step, the substrate device is pivoted into a temperature control state, in which the second chamber is arranged above the first chamber and the substrate platform forms the floor of the second chamber. The cultivation liquid flows out of the first chamber so that, advantageously, the cells still adhering to the cultivation surface remain covered only with a thin liquid film formed due to the surface tension of the residual cultivation liquid. This minimizes the volume of the biological sample that is to be subjected to cryopreservation. In the temperature control state the cooling medium, e.g. liquid nitrogen, is filled into the second chamber. The cooling medium covers the upward-facing back side of the substrate platform so that the latter is instantly cooled together with the biological sample arranged on the cultivation surface.

A second variant of the method according to the invention affords a "hanging-droplet" cultivation and a vitrification of cells in the hanging droplet. This results in a cryopreservation of biological cells in a non-adherent state. The biological cells are frozen in hanging droplets. For this purpose, in a first partial step, the substrate device is placed in the temperature control state, in which the second chamber is above the first chamber and the substrate platform forms the floor of the second chamber. The cultivation surface of the substrate platform is aligned horizontally, the normal to the cultivation surface pointing vertically downwards, i.e. in the direction of gravity. Hanging droplets of the cultivation liquid are applied to the cultivation surface and biological cells are placed therein individually or in groups. Optionally, before freezing, provision can be made to cultivate the biological cells in the hanging droplets. In a second partial step, as in the first embodiment of the method according to the invention, the second chamber is filled with the cooling medium so that the substrate platform and the biological sample are rapidly frozen.

The substrate device according to the invention also offers advantages in the recovery of the cryopreserved cells. The second chamber can be used to thaw the biological sample. For this purpose a heating medium, for example water at a predetermined thawing temperature of e.g. 37° C., is filled into the second chamber when the substrate device is in the temperature control state. The substrate platform carrying the biological sample is heated by the heating medium until the biological sample is thawed. The cells can then be removed from the first chamber or subjected to further cultivation therein.

Further advantages of the invention are summarized below. The invention makes it possible to combine the advantages of adherent cryopreservation with those of vitrification by liquid nitrogen. As the cells can be cryopreserved in the adherent state, they do not need to be treated with enzymes, such as trypsin or collagenase, before vitrification, for instance to detach the cells from the substrate, and the colonies do not have to grow again, after thawing, before further culture is possible. Also, the cell-cell contacts are maintained in their original form, so the stress occurring on the cells is reduced even more.

Moreover, the survival rates and the functionality of the cells after cryopreservation are superior or comparable to those of in-straw vitrification. An advantage over the straw, however, is the possibility of preserving a large quantity of cells at one time. For example, a plurality of colonies can easily be vitrified in a simple manner by enlarging the cultivation surface of the substrate device. Also, the incubation times in which cryoprotective agents are introduced, optionally in high concentrations, are precisely definable since each cell colony comes into contact with the respective media simultaneously rather than at different times, as in the case of the straw, where each colony is treated individually.

Another advantage of the method according to the invention is that it can easily be automated. The samples do not have to be transferred from one cryomedium to the next by laborious manual pipetting and then sucked into the straw. Instead, the medium can be changed simply by suction or even by automatic rotation of the substrate. The ease of handling of the system ensures that the success of the preservation does not depend on the individual expertise and skill of the operator, but that the preservation can be carried out universally with similar success.

The danger of contamination of previous adherent vitrification methods is minimized by the "two-chamber system" according to the invention. Because there is at all times a physical barrier, in the form of the cultivation surface, between the cultivation compartment and the nitrogen compartment, no contact takes place between cell material and potentially non-sterile nitrogen. Moreover, the cultivation compartment (first chamber) can be separated from the surroundings, in particular protected from ambient air, by a cover. This simplifies the use of the system for therapeutic purposes and it is not necessary to use sterile nitrogen for vitrification or for storage in a tank.

The general physical conditions for successful vitrification, such as minimized sample volume and maximized surface-to-volume ratio for the fastest possible cooling rate, are favored by several aspects of the invention. Firstly, adherent cultivation and vitrification in the hanging state ("overhead") results in the formation of a minimal liquid film over the cells. Excess medium flows out downwards and therefore does not lead to unwanted enlargement of the sample volume. Hence it is always possible to use sufficient cryomedium for incubation without the danger of too large a volume for vitrification. By virtue of the minimal liquid film, the toxic cryomedium can also be diluted easily with small amounts of a washing medium after thawing. Cell damage due to toxic cryomedia is thereby minimized. Moreover, the flat shape of the grown sample, e.g. cell colony, has a positive influence on the cooling rate. The distance between cooling medium and cells is minimal and the surface-to-volume ratio of the two-dimensional cell colony is greater than e.g. in the straw. In addition, the cell colonies can be cryopreserved in co-culture with other cell types. This dispenses with a labor-intensive preparation of the co-culture after thawing, and the time spent by the cells outside the co-culture is minimized. This advantage is particularly pronounced in the co-culture between hESC and mouse feeder cells.

The possibility of using different cultivation surfaces enables the substrate device according to the invention to be manipulated as a function of use and cell type. The success of vitrification can be further maximized by improved thermal conduction of the surface. A special anchoring means for different culture surfaces enables them to be exchanged as a function of use. Thermally induced volume changes in the materials used can be absorbed by a flexible buffer zone between the culture surface and its holder. This allows materials with different coefficients of thermal expansion to be used for the substrate. A possible alternative is to use the same material for the culture surface and the rest of the substrate device. The volume changes are therefore the same and no stresses occur in the material.

As the formation of a meniscus increases the volume of media over the cells in the marginal region of the substrate, the angle and the material in the marginal region can be adapted so that a meniscus is no longer formed. This favors optimization of the vitrification of the cells even in the marginal region.

BRIEF DESCRIPTION OF THE DRAWINGS

Further details and advantages of the invention are described below with reference to the attached drawings, which show in.

DETAILED DESCRIPTION OF THE INVENTION

Embodiments of the invention are explained below with reference to the features of the substrate device and the cryopreservation apparatus and to the steps of the cryopreservation method. Details of the cultivation of biological cells in the adherent state or in hanging droplets, of the cultivation media, of the use of cryoprotective agents, of the treatment protocols, of the monitoring of preservation and of the handling of cooling or heating media are not described if they are known from conventional techniques. The substrate device and the cryopreservation apparatus are illustrated by way of example with the aid of schematic sectional views with a vertical cutting plane (perpendicular to the horizontal). The geometric shape of the substrate device or cryopreservation apparatus, including in spatial directions that differ from the illustration, can be chosen as a function of the desired use of the invention. For example, the substrate device can have a circular or rectangular shape in horizontal projection (perpendicular to the cutting plane in the Figures). Moreover, the structure formed by the first and second chambers can have a cylindrical shape (like a can). When a large number of first chambers for sample cultivation are combined with a common chamber for the temperature control medium, the shape and arrangement of the first chambers can likewise be chosen as a function of the conditions of the desired uses.

Figure 1:
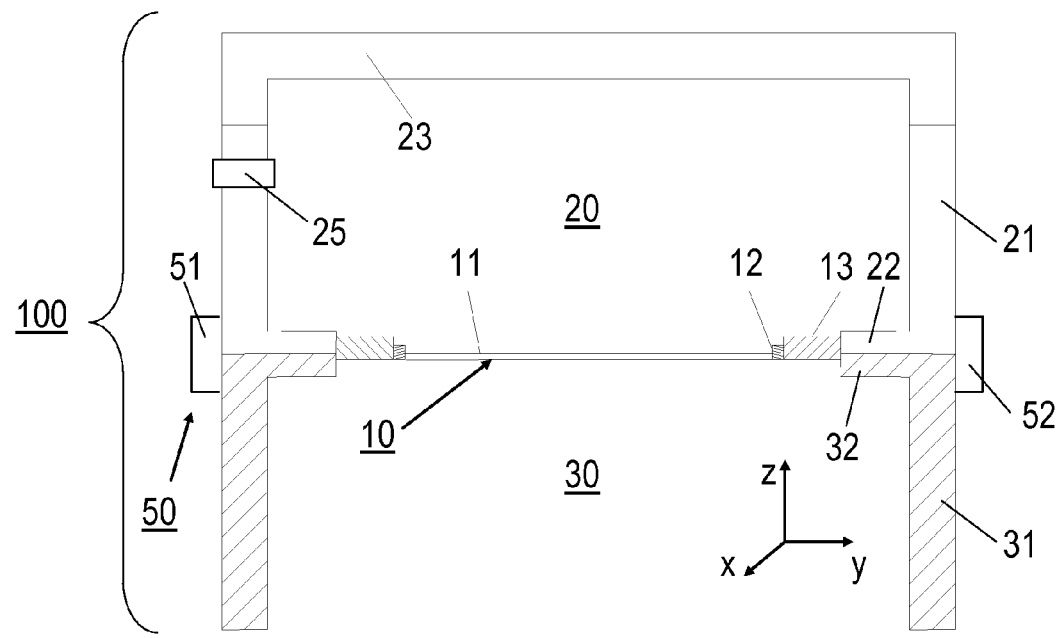
FIG. 1 a schematic sectional view of a first embodiment of the substrate device according to the invention in the cultivation state.

The embodiment of the substrate device 100 according to the invention shown in FIG. 1 comprises the substrate platform 10, a first chamber 20 and a second chamber 30. The substrate platform 10 forms a separating wall between the interior of the first chamber 20 and the interior of the second chamber 30.

The substrate platform 10 is connected to a chamber wall 21 of the first chamber 20 via a substrate holder 12 and a compensating section 13. The chamber wall 21 of the first chamber 20 is in the shape of a hollow cylinder whose cylindrical axis forms the axis of symmetry of the substrate device 100 and is orientated in the vertical direction (z-direction) in the cultivation and temperature control states (cf. below). At its end facing towards the second chamber 30, the cylindrical chamber wall 21 of the first chamber 20 has a projection 22 to which the compensating section 13 is connected. At the opposite end, facing away from the second chamber 30, the chamber wall 21 of the first chamber 20 has a seat for a cover 23. The cover 23 can be coupled with the chamber wall 21 of the first chamber 20 so as to exclude gas exchange between the interior of the first chamber 20 and the surroundings of the substrate device 100.

The second chamber 30 comprises a chamber wall 31 whose shape and size are adapted to the shape and size of the first chamber 20. In the example shown, the chamber wall 31 of the second chamber 30 is also in the shape of a hollow cylinder with a projection 32 protruding radially inwards at the edge facing towards the first chamber 20. The compensating section 13 of the substrate platform 10 can be connected exclusively to the projection 22 of the first chamber, to both the projections 22, 32, as shown, or exclusively to the projection 32 of the second chamber 30. The second chamber 30 is open on the side facing away from the substrate platform 10. However, in a modified variant, a cover can also be provided on the second chamber 30.

The chamber walls 21, 31 of the first and second chambers 20, 30 can be made of different materials, e.g. plastic and/or metal, and be connected to each other at the projections 22, 32. Alternatively, the chamber walls 21, 31 can be made in one piece as an integral component, e.g. from plastic or metal.

The substrate platform 10 comprises a flat sheet of glass, plastic or metal in the shape of a circular disk. The upper side of the glass sheet, facing towards the first chamber 20, forms the cultivation surface 11, which consists e.g. of the exposed glass surface or of a glass surface carrying a biocompatible surface layer. The cultivation surface 11 is adapted for receiving the sample to be preserved, which comprises at least one biological cell (cf. FIG. 3), and can comprise in particular a surface provided with a cell culture (e.g. hESCs, MEFs, iPS cells or other cell types that grow adherently) and/or of a hydrophilic surface.

The substrate holder 12 is an annular frame in which the substrate platform 10 is detachably positioned. The frame is configured for liquid-tight coupling of the substrate platform 10 and comprises e.g. a rest for the substrate platform and a circumferential sealing lip for tightly fixing the applied substrate platform 10. The substrate platform 10 can be exchanged, e.g. for the purpose of adapting to a specific cultivation task, by lifting the sealing lip and removing the substrate platform 10. The substrate holder 12 is preferably made of a non-rigid plastic, particularly silicone rubber, or metal.

The compensating section 13 is an expansion joint for compensating dimensional changes in the parts of the substrate device 100 as a function of temperature. The compensating section 13 is in the shape of e.g. an annular disk, which is made of materials that are matched to the adjacent materials, on the one hand of the substrate platform 10 and/or the substrate holder 12, and on the other hand of the projection 22, 32 and/or the chamber wall 21, 31. The materials are chosen so that their thermal expansions or contractions due to temperature change complement or offset each other. For example, if the material of the chamber wall 21, 31 contracts more than that of the substrate platform 10 (i.e., in this example, contract in the cold even more than the chamber wall 21, 31), the compensating section 13 should compensate this. Departing from the illustration, the substrate holder 12 and the compensating section 13 can be made in one piece as an integral component. In this case this component serves as both substrate holder and compensating section.

In a practical embodiment, the substrate device 100 has e.g. the following dimensions: diameter of the substrate platform: 20 mm, thickness of the substrate platform: 180 μm (e.g. of the μ-dish type from the manufacturer ibidi GmbH, Germany), external diameter of the substrate device 100 in the x-y plane: 35 mm, thickness of the first and second chamber walls 21, 31: 3 mm, height of the first and second chamber walls 21, 31 in the z-direction: 10 mm each, height of the cover 23 in the z-direction: 4 mm. The stated dimensions are only examples; those skilled in the art can choose the dimensions as a function of the requirements of a concrete use.

Figure 2:
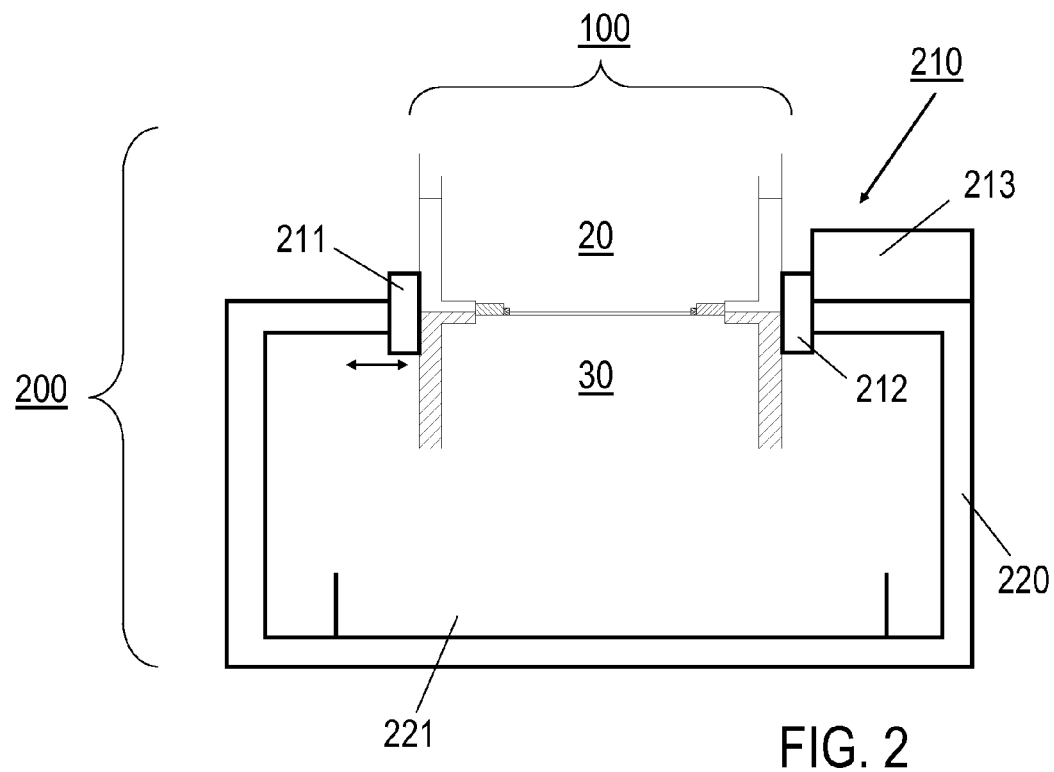
FIG. 2 a schematic sectional view of an embodiment of the cryopreservation apparatus according to the invention.

Arranged on the outer side of the first and second chambers 20, 30, e.g. in a plane with the substrate platform 10, as shown, there is a chamber holder 50 which is configured for receiving the substrate device 100 in the cryopreservation apparatus, e.g. according to FIG. 2. The chamber holder 50 comprises e.g. two spigots 51, 52 projecting radially outwards on the cylindrical outer side of the substrate device 100, which are arranged opposite each other along a common line of reference.

In a variant of the invention, the substrate device 100 can be provided with a pressure equalizing valve 25, which is shown schematically in FIG. 1. The pressure equalizing valve 25 is inserted in the chamber wall 21 or the cover 23 and is designed for equalizing any excess pressure in the first chamber relative to the surroundings.

FIG. 2 schematically shows an embodiment of the cryopreservation apparatus 200 according to the invention, which is adapted for receiving a substrate device 100, e.g. according to FIG. 1, and for implementing the cryopreservation method according to the invention (cf. below). The cryopreservation apparatus 200 comprises a rotating device 210, with which the substrate device 100 can be hold and rotated, and a supporting frame 220, which is configured for a stable positioning of the rotating device 210 with the substrate device 100 on a working surface (not shown), e.g. a bench top. The supporting frame 220 is a component made e.g. of plastic and/or metal, on whose lower side a trough 221 can be provided for receiving outflowing cultivation liquid or outflowing temperature control medium.

The rotating device 210 comprises pivot bearings 211, 212, which are arranged, with a distance between them, on opposite extension arms of the supporting frame 220. The pivot bearings 211, 212 receive the spigots 51, 52 of the chamber holder 50 (cf. FIG. 1). For this purpose it is possible e.g. for one of the pivot bearings 211 to be elastically displaceable in the axial direction (cf. double arrow) so that, when the substrate device 100 is inserted in the pivot bearings 211, 212, the distance between the latter can be increased. The rotating device 210 is moreover shown with an optional device unit 213, illustrated schematically. The drive unit 213 comprises e.g. an electric motor, which is designed to rotate the substrate device 100 and is connected to the substrate device 100 via power transmission elements, e.g. gears.

Figure 3:
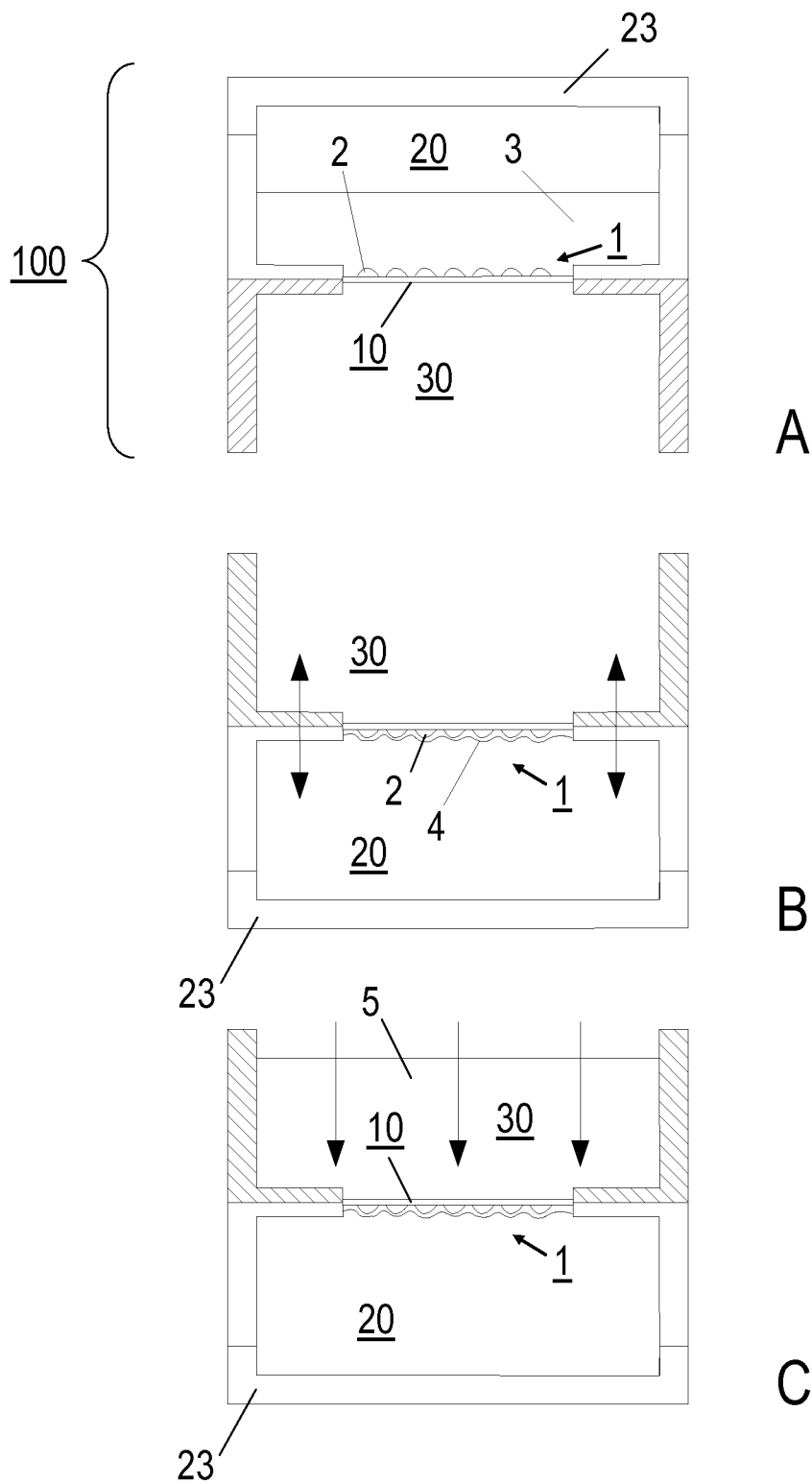
FIG. 3 (A-C) steps of a cryopreservation method in a preferred embodiment of the invention.

FIG. 3 schematically illustrates steps of the method for the cryopreservation of a biological sample 1 including biological cells 2, in an embodiment of the invention, wherein the biological cells 2 form an adherent cell culture on the cultivation surface of the substrate platform 10. FIG. 3A shows the provision of the biological sample 1 on the cultivation surface of the substrate platform 10 in the first chamber 20 of the substrate device 100 (cf. FIG. 1), the biological cells 2 being surrounded by a cultivation liquid 3. In this embodiment of the invention, the cultivation of the adherent cells takes place in the cultivation state illustrated, in which the first chamber 20 is above the second chamber 30. Accordingly, the first chamber 20 can be filled with the cultivation liquid 3, while the second chamber 30 is open at the bottom and empty. The cultivation liquid 3 has a composition chosen as a function of the cell types and the concrete use of the invention, and comprises nutrient medium and at least one cryoprotective agent, e.g. a composition of 20% DMSO, 20% ethylene glycol and 300 mM trehalose.

The cultivation of the biological cells 2 takes place according to a predetermined cultivation protocol specific to cell type. Here it is possible for the cover 23 of the substrate device 100 to be hermetically closed or open. The ability of the first chamber 20 to be closed with the cover 23 is of particular advantage while the first chamber 20 is being transported. For example, the cultivation can take place in a different location from the cryopreservation, e.g. in an incubation apparatus. For subsequent cryopreservation the substrate device 100 can be transported, with the cover 23 closed, to e.g. a cryopreservation apparatus according to FIG. 2.

In a concrete, experimentally tested example the cells 2 consist of human embryonic stem cell colonies (hESC colonies) surrounded by a monolayer of mouse fibroblasts, while the cultivation liquid 3 is composed of 20% DMSO, 20% ethylene glycol and 300 mM trehalose in standard hESC culture medium. The cultivation according to FIG. 3A can extend over hours or days in the substrate device 100. Alternatively, the cultivation of the biological cells 2 on the substrate platform 10 can take place first in a separate incubation apparatus. After a desired cultivation result has been achieved, the substrate platform 10 can be inserted in the substrate device 100.

In another partial step, according to FIG. 3B, the substrate device 100 is rotated through 180° about a horizontal axis of rotation. The substrate device 100 is then in a temperature control state in which the second chamber 30 is above the first chamber 20. The sample 1 is suspended in the adherent state from the downward-facing cultivation surface of the substrate platform 10. By virtue of the surface tension of the cultivation liquid 3, a liquid film 4 is also maintained in the temperature control state according to FIG. 3B and covers the cells. Advantageously, the cells 2 therefore remain in contact with the cultivation liquid in the form of the liquid film 4, while the volume of the cultivation liquid is minimized by the formation of the film. This assists rapid freezing of the sample 1 when a cooling medium 5 is subsequently introduced into the second chamber 30 (cf. FIG. 3C).

The cryopreservation of the sample 1, in particular its vitrification, is effected by filling a cooling medium 5, e.g. liquid nitrogen, into the second chamber 30 (cf. arrows in FIG. 3C). Heat exchange occurs through the substrate platform 10, which simultaneously forms the separating wall to the interior of the first chamber 20, so the sample 1 is rapidly cooled to −196° C. The sample 1 is vitrified and remains stable if the temperature is maintained below −130° C. The stability of the sample is assured in particular if the cooling medium 5 is maintained in the second chamber. In particular, this allows practically unlimited transport of the cryopreserved sample 1 provided that the cooling medium 5 is refilled. If the substrate device 100 is stored in liquid nitrogen vapor, e.g. in a gas phase in a nitrogen tank, the cooling medium 5 in the second chamber 30 can gradually evaporate, although the sample 1 also remains stably vitrified in the gas phase at around −170° C.

FIGS. 3B and 3C show the temperature control state of the substrate device 100 with the first chamber 20 closed. Accordingly, when the substrate device 100 is rotated from the cultivation state to the temperature control state, the residual cultivation liquid 3 is retained in the first chamber 20 by the cover 23. Departing from the representation, the cover 23 can be removed in the temperature control state so that all the cultivation liquid 3, except the liquid film 4, flows out.

Whereas FIG. 3 refers to the cultivation and cryopreservation of adherent cells by way of example, the cultivation and cryopreservation can alternatively be carried out with biological cells in hanging droplets ("hanging-droplet" cultivation). In this case the substrate device is already placed in the temperature control state for the cultivation, the second chamber 30 being arranged above the first chamber 20 and the cultivation surface of the substrate platform facing downwards, i.e. in the direction of gravity. Droplets of the cultivation liquid with suspended cells hang from the cultivation surface. The introduction and/or exchange of the cultivation liquid, including the cryoprotective agents, is effected by methods known from conventional hanging-droplet cultivation. For vitrification of the sample, the cooling medium is introduced into the second chamber so that the droplets containing the cells are rapidly frozen.

Figure 4:
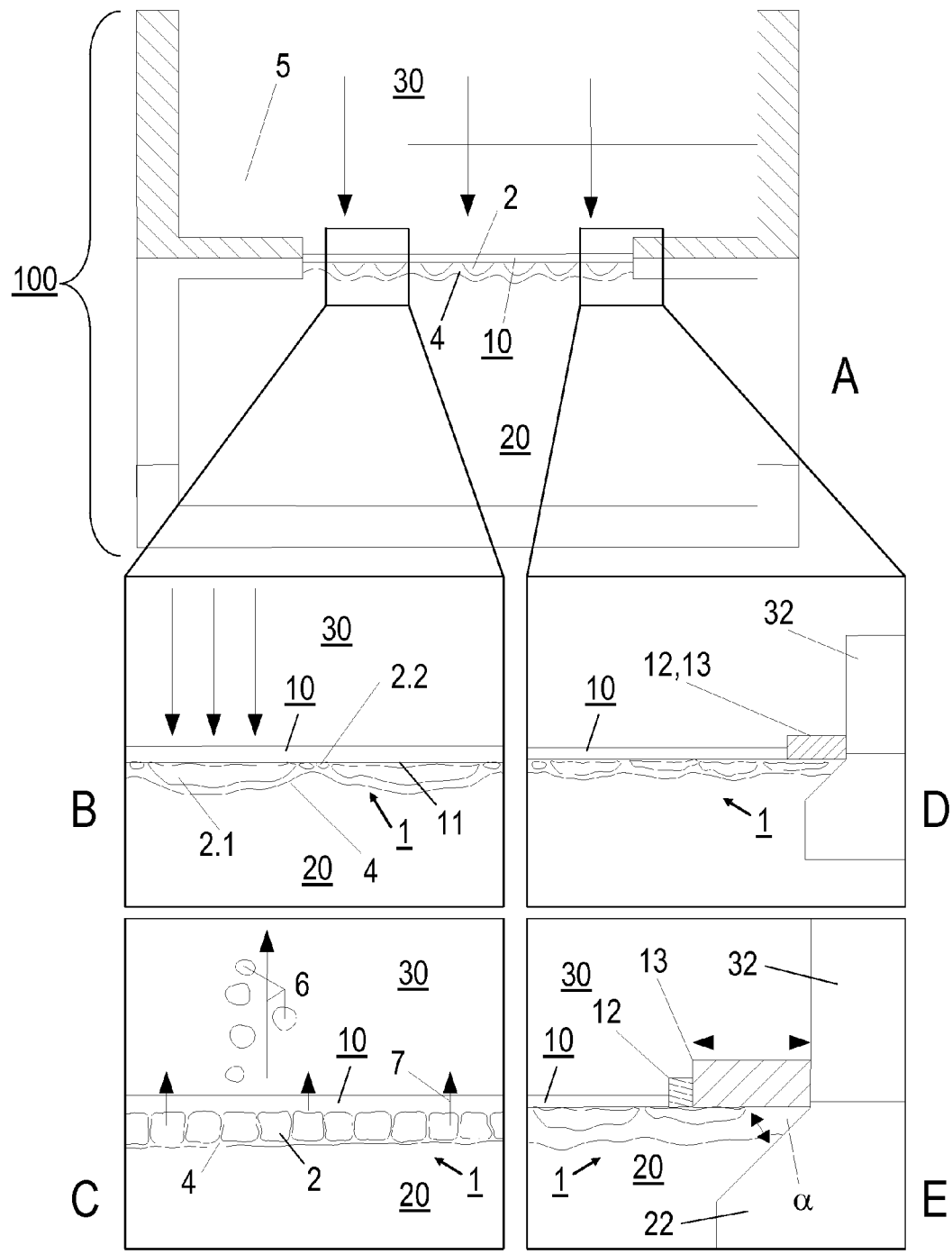
FIG. 4 (A-E) enlarged sectional views of the substrate platform of the substrate device according to FIG. 1.

FIG. 4 shows further details of the substrate device 100 in the temperature control state. FIG. 4A shows the substrate device 100, as in FIG. 3C, with the first chamber 20, the second chamber 30 and the substrate platform 10 forming a separating wall between them. The biological cells 2 are arranged in an adherent manner on the downward-facing cultivation surface of the substrate platform 10 and covered with the liquid film 4. The second chamber 30 is filled with the cooling medium 5 from above (cf. arrows) so that the biological cells 2 are rapidly cooled and vitrified.

FIG. 4B shows an enlarged cutout of the substrate platform 10 on whose cultivation surface 11, facing downwards towards the first chamber 20, the sample 1 containing biological cells, particularly cell groups 2.1 and individual cells 2.2, of different types is arranged. For example, the larger cell groups 2.1 (cell colonies) consist of human embryonic stem cell colonies, while the cells 2.2 comprise of mouse embryonic fibroblasts that form a cellular monolayer. The cell groups 2.1 and cells 2.2 are adherently bound to the cultivation surface 11.

When the cooling medium 5 is filled into the second chamber (cf. arrows in FIG. 4B), the substrate platform 10 is rapidly cooled. As the cooling medium 5 is filled into the second chamber 30 from above, the Leidenfrost phenomenon can be minimized. Gas bubbles 6, which are formed as the cooling medium 5 impinges on the substrate platform 10 (cf. modified illustration in FIG. 4C), move in the opposite direction to that of gravity, i.e. upwards, the corresponding volume being replaced by inflowing cooling medium. The insulating effect of gas bubbles that arises in conventional cryopreservation methods can therefore be minimized.

FIG. 4C further illustrates that the distance between the cooling medium 5 and the cells 2 is minimized by the small thickness of the substrate platform 10. The heat of the sample 1, containing cells 2 and the liquid film 4, flows rapidly towards the cooling medium 5 (cf. arrows 7 in FIG. 4C).

Variants of the fixing of the substrate platform 10 to the walls of the first and second chambers 20, 30 are shown schematically in FIGS. 4D and 4E. The substrate platform 10 is fixed e.g. with the substrate holder 12 and the compensating section 13 (shown as an integral component) to the projection 32 of the wall of the second chamber 30 (FIG. 4D). The compensating section 13 makes it possible to avoid mechanical stresses on the substrate platform 10 and the substrate holder 12, in particular when the substrate platform 10 and the other walls of the first and second chambers 20, 30 have different coefficients of thermal expansion.

FIG. 4E schematically illustrates that the projection 22 of the wall of the first chamber 20 forms a circumferential protrusion facing towards the interior of the chamber 20, which partially projects beyond the substrate platform 10, the substrate holder 12 and/or the compensating section 13. The angle α between the plane of the substrate platform 10 and the edge of the projection 22 along the protrusion is less than 90°. Advantageously, this ensures that no meniscus is formed between the sample 1 and the projection 22, but that the thickness of the sample 1 remains unchanged up to the projection 22. Advantageously, this even ensures that the cryopreservation conditions in the marginal region of the sample 1 are the same as those in the middle of the substrate platform 10, affording optimal vitrification of the cells 2.

Figure 5:
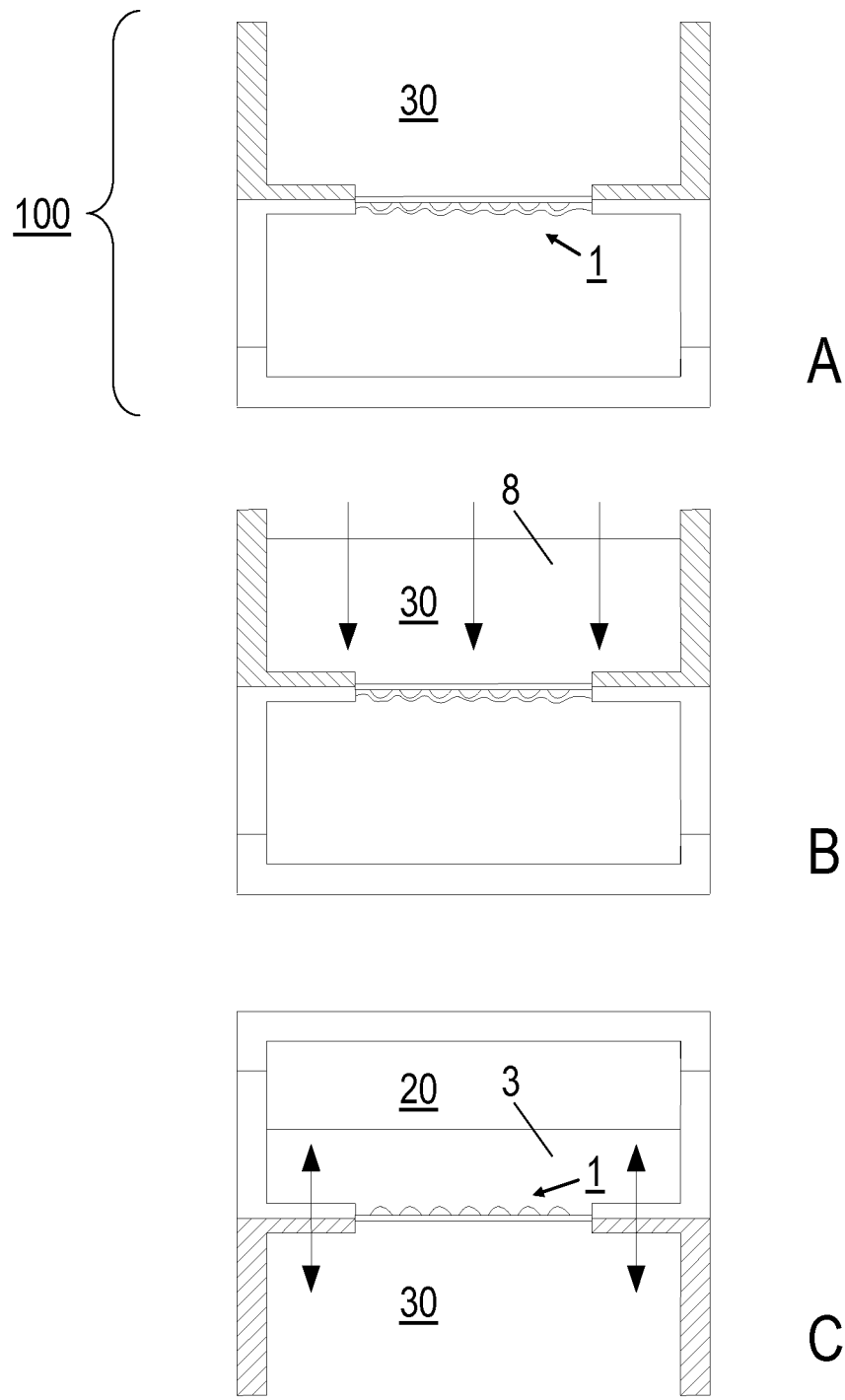
FIG. 5 (A-C) steps of a recovery of a biological sample after cryopreservation.

FIG. 5 schematically shows the recovery of the sample 1 after the cryopreservation. As the liquid cooling medium, e.g. liquid nitrogen, evaporates on storage in the gas phase of a nitrogen tank, the second chamber 30 is typically empty during the cryopreservation (FIG. 5A). In this situation the substrate device 100 can be removed from the nitrogen tank in order to thaw the sample 1. This is done by filling a heating medium 8, e.g. water at a temperature of 37° C., into the second chamber 30 from above (cf. arrows in FIG. 5B). The thawing of the sample can take place rapidly, like the cryopreservation, whereby the formation of ice crystals in the sample 1 is also avoided during thawing.

Then, according to FIG. 5C, the substrate device 100 is rotated back to the cultivation state (cf. double arrows), in which the first chamber 20 is arranged above the second chamber 30. The second chamber 30 is emptied, while more cultivation liquid 3 is filled into the first chamber 20. With the cultivation liquid 3 the sample 1 is e.g. washed and cultivated further. Additional processing steps, e.g. passages or further vitrification, can follow.

Alternatively to the steps shown in FIG. 5, provision can be made, on thawing, for the heating medium to be filled into the first chamber 20 in the cultivation state of the substrate device 100. In this case the heating medium can be a cultivation liquid heated to 37° C.

Figure 6:
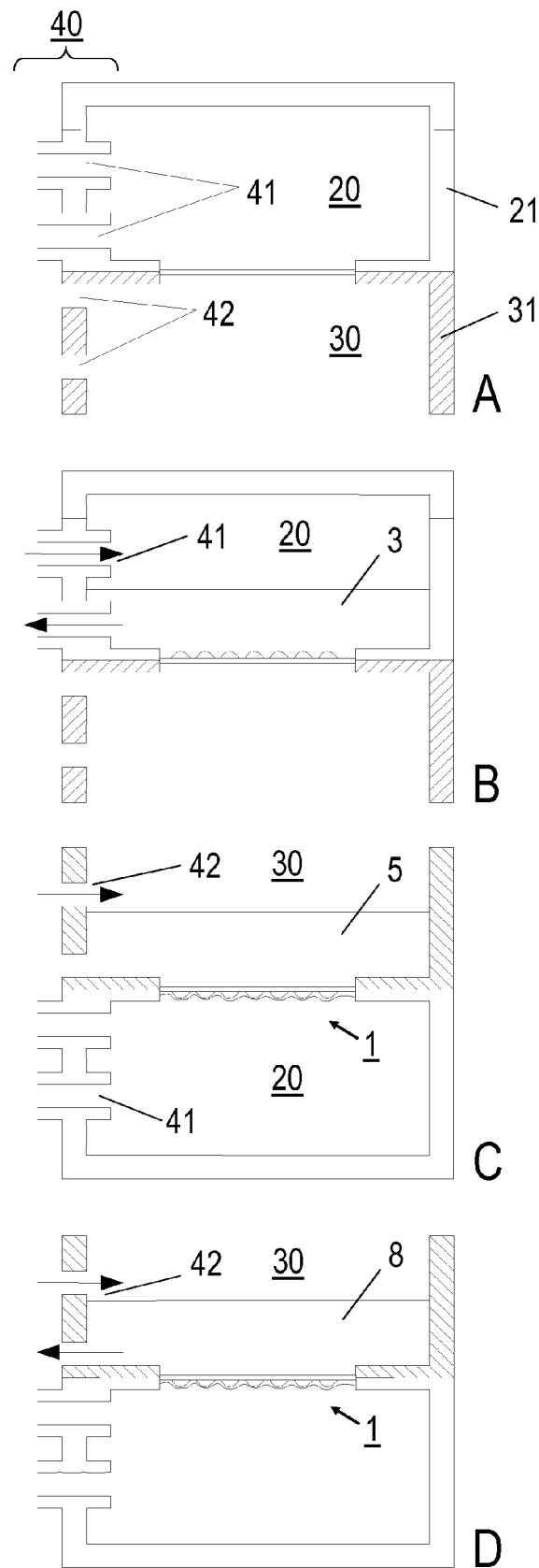
FIG. 6 (A-D) a schematic sectional view of another embodiment of the substrate device according to the invention with a delivery device.

In another embodiment of the invention, the substrate device 100 can be provided with a delivery device 40, such as that shown by way of example in FIG. 6. In the example shown, the delivery device 40 comprises a large number of media lines 41, 42, respectively connected to the first chamber 20 or the second chamber 30. The media lines 41, 42 are e.g. tubes or pipes (not shown in full) connected to liquid reservoirs and pumps, and they allow in particular an automated delivery of cultivation liquids into the first chamber 20 and an automated delivery of cooling or heating media into the second chamber 30. The media lines 41, 42 (or at least the illustrated ends or connections of the media lines) are integrated into the walls 21, 31 of the first and second chambers 20, 30. Alternatively, media lines can also be connected to a cover of the first or second chamber.

According to FIG. 6B, at least one cultivation liquid 3 is introduced in the cultivation state through the media lines 41 of the first chamber 20. For example, according to a predetermined cultivation protocol, a succession of nutrient media and/or cryoprotective agents of predetermined composition and/or concentration can be introduced into the first chamber 20.

For freezing the sample 1, the substrate device is rotated into the temperature control state, in which the second chamber 30 is above the first chamber 20 (FIG. 6C). In this situation cooling medium is filled into the interior of the second chamber 30 via the media lines 42 of the second chamber 30. The filling level of the cooling medium 5 in the second chamber 30 can be adjusted by suitably controlling the inflow and outflow of cooling medium. The first chamber 20 is simultaneously emptied via the media lines 41 of the first chamber 20. For thawing the sample 1, provision is made, according to FIG. 6D, for the second chamber 30 to be filled with a heating medium 8, e.g. water, via the media lines 42.

Figure 7:
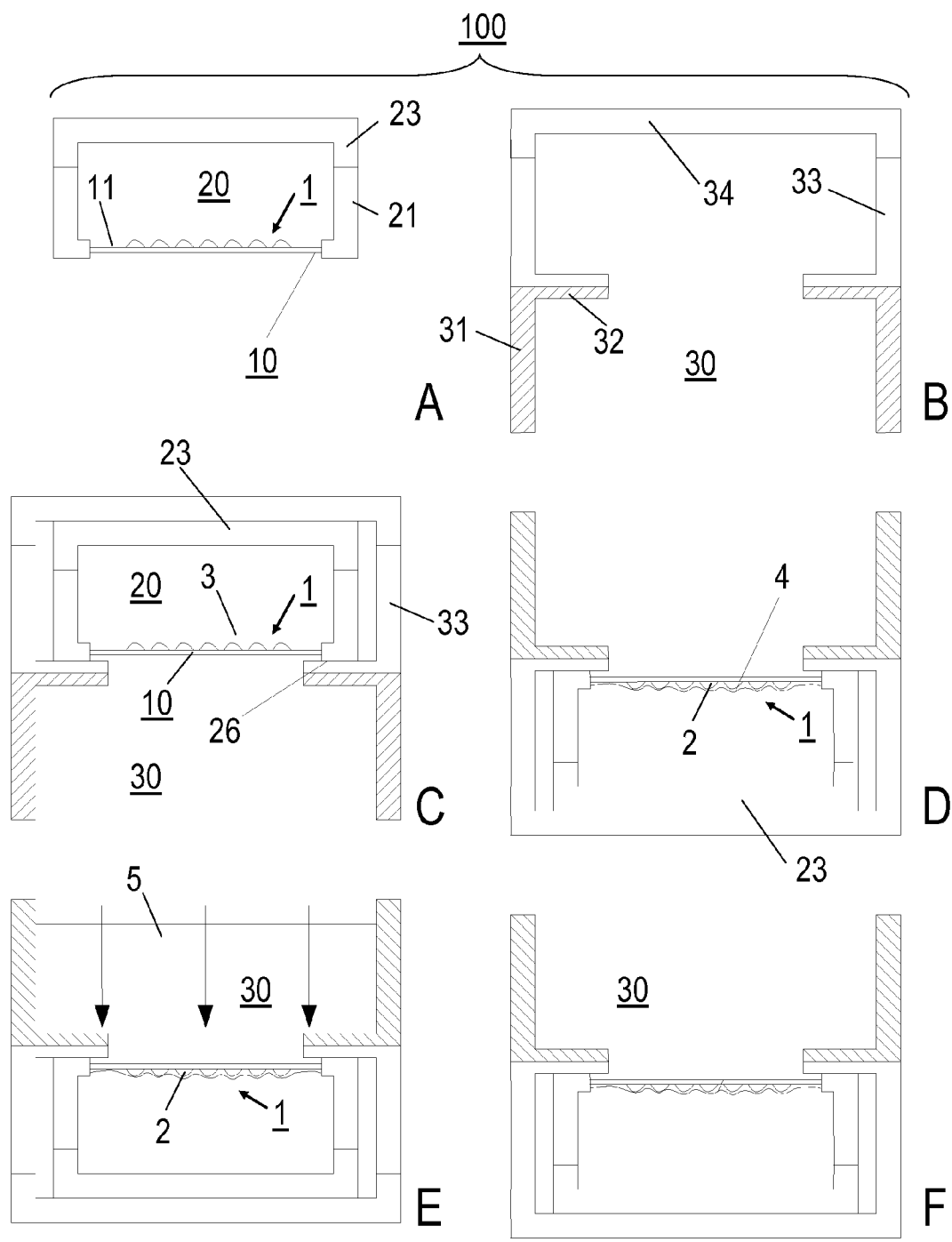
FIG. 7 (A-F) schematic sectional views of another embodiment of the substrate device according to the invention with a chamber frame.

Departing from the embodiment according to FIG. 1, the first and second chambers 20, 30 of the substrate device 100 according to the invention can be detachably connected to each other, as shown by way of example in FIG. 7. The first chamber 20 (FIG. 7A) is a container whose interior is surrounded by the substrate platform 10, the chamber wall 21 and the cover 23. The cultivation surface 11 of the substrate platform 10 is arranged facing towards the interior of the first chamber 20 for receiving the sample 1 in the adherent state or in hanging droplets, while the surface of the substrate platform 10 that is opposite the cultivation surface 11 is exposed outwards. The second chamber 30 (FIG. 7B) has a structure comprising a chamber wall 31 with a projection 32 protruding radially inwards, and a chamber frame 33, which is configured for detachably receiving the first chamber 20. The chamber frame 33 is a cylindrical seat whose internal diameter is equal to the external diameter of the first chamber 20. On the side facing away from the second chamber 30, provision is made for a frame cover 34 with which the first chamber 20 can be fixed in the chamber frame 33. The side of the chamber frame 33 that faces towards the second chamber 30 has an opening through which the substrate platform 10 is exposed towards the interior of the second chamber 30.

The two-part construction of the substrate device 100 shown in FIGS. 7A and 7B has the advantage that the second chamber 30 (the vitrification chamber) can be used several times as a casing for the first chamber 20 (the cultivation chamber). The shape of the first chamber 20 can be adapted for optimal cultivation, e.g. in an incubation apparatus. The second chamber 30 is not coupled with the first chamber 20 until the desired cryopreservation is to be carried out. Moreover, commercially available cultivation substrates can be used for the first chamber in cases where the second chamber 30 with the chamber frame 33 is suitably adapted to the geometry of the particular culture substrate.

The embodiment of the substrate device 100 according to FIGS. 7A and 7B has the advantage that the cultivation and observation, e.g. microscopic investigation, of the sample 1 can take place without the second chamber 30 and without the chamber frame 33. This offers additional degrees of freedom in the preparation of the sample 1 for the cryopreservation and/or the choice of suitable samples containing biological cells at a predetermined cultivation stage.

FIGS. 7C to 7F show the steps of the cryopreservation according to the invention using the substrate device 100 according to FIGS. 7A and 7B. According to FIG. 7C the first chamber 20, with the substrate platform 10, the sample 1 and the cultivation liquid 3, is inserted in the chamber frame 33 and fixed. If necessary, a seal (not shown) can be provided on the contact surface 26 of the first chamber 20 and on the chamber frame 33 in order to prevent the cooling medium penetrating from the second chamber 30 into the surroundings of the first chamber 20, in particular its cover 23.

Before vitrification starts, the substrate device is rotated through 180° relative to the plane of the substrate platform 10 so that the sample 1 with the cells 2 and the liquid film 4 is hanging downwards. The excess cultivation liquid is caught in the downward-facing cover 23 of the first chamber, or led away via a media line (not shown) (FIG. 7D).

This is followed by the introduction of the cryomedium 5, e.g. liquid nitrogen, into the second chamber 30 (FIG. 7E). As a result, heat is rapidly transported away from the substrate platform 10 and the sample 1, and the sample 1 containing the biological cells 2 is vitrified. Further storage can take place in the gas phase above liquid nitrogen in the nitrogen tank, it being possible for the liquid cooling medium to evaporate out of the second chamber (FIG. 7F).

Figure 8:
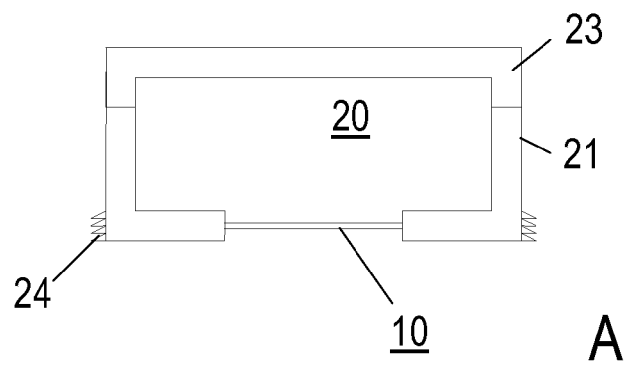
FIG. 8 (A-C) schematic sectional views of another embodiment of the substrate device according to the invention with a screw joint.
Figure 8:
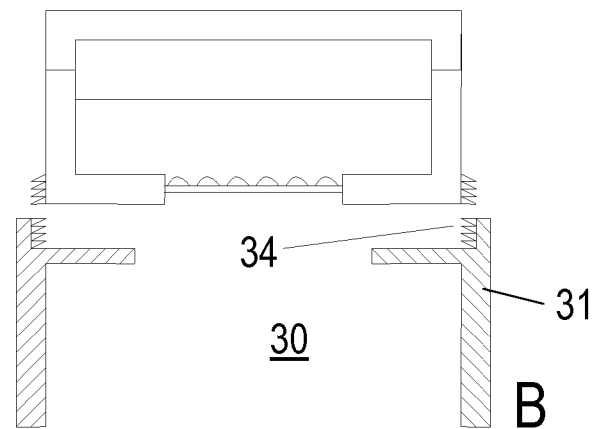
Figure 8:
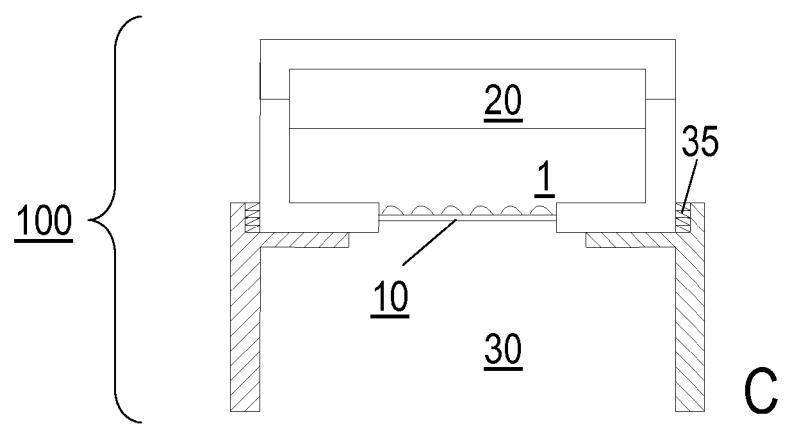

Another variant of the multipart substrate device 100 is illustrated in FIG. 8. The first chamber 20, with the substrate platform 10, the chamber wall 21 and the cover 23, is constructed as a closable container. On the outer side of the first chamber 20, in particular on the outer side of the chamber wall 21, an external thread 24 is provided which cooperates with an internal thread 34 on the chamber wall 31 of the second chamber 30 to form a screw joint 35 (FIG. 8B). For reception in the cryopreservation apparatus 200 (FIG. 2), the second chamber 30 can have a chamber holder on its outer side, as described above with reference to FIG. 1. In the assembled state of the first chamber 20 and the second chamber 30 (FIG. 8C), the substrate platform 10 is exposed towards the interior of the second chamber 30, while the inner side of the substrate platform 10, as described above, forms the cultivation surface for the sample 1 in the interior of the first chamber 20. In the assembled state the substrate device 100 can be used for the vitrification of the sample 1, as described above.

Figure 9:
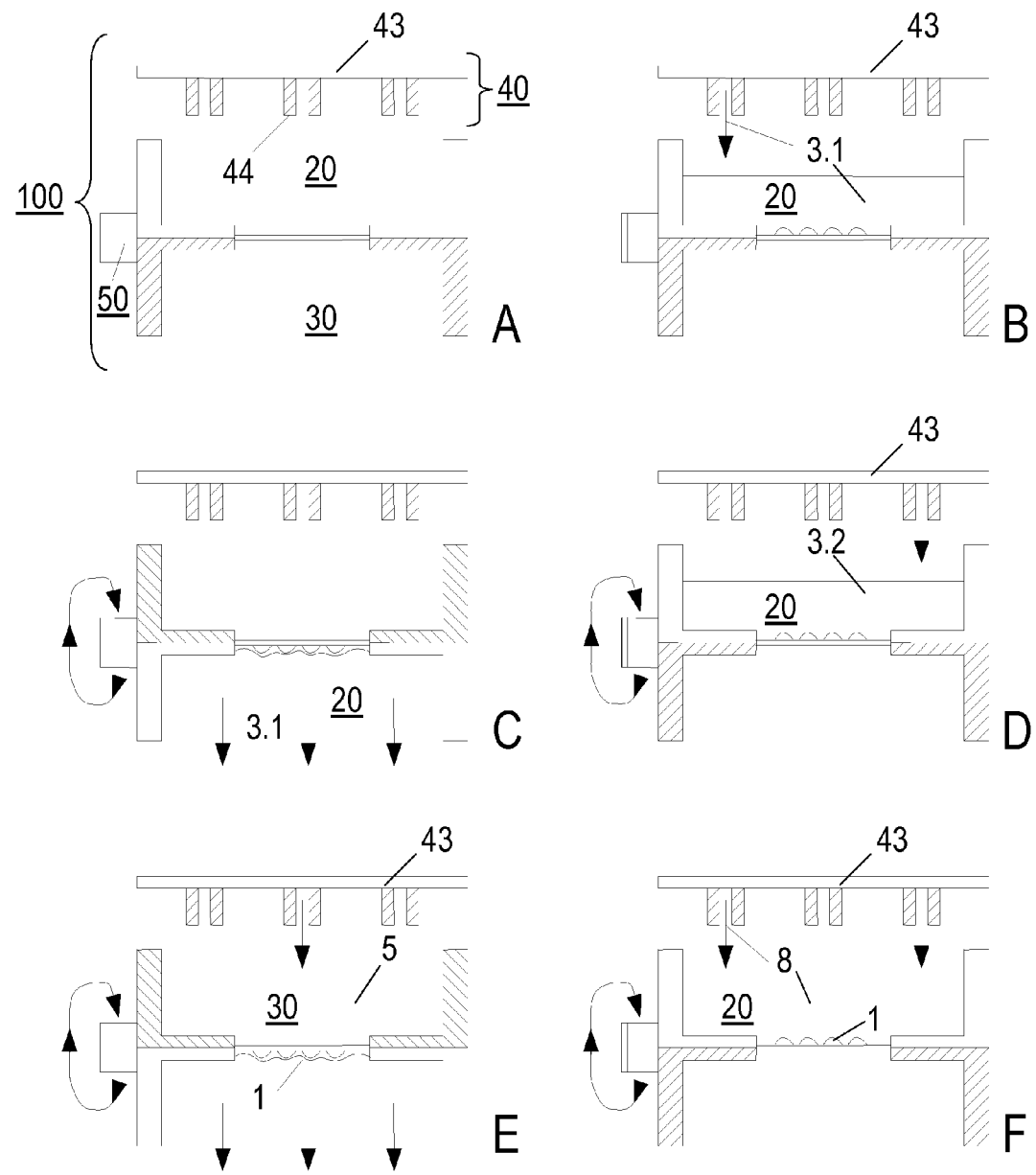
FIG. 9 (A-F) schematic sectional views of another embodiment of the substrate device according to the invention with a microfluidic unit.

FIG. 9 shows another embodiment of the substrate device 100 according to the invention, where the delivery device 40 for delivering the at least one cultivation liquid consists of a microfluidic unit 43 (or media delivery chip). The microfluidic unit 43 contains microfluidic elements 44, e.g. media lines, valves, liquid reservoirs and/or pumps. With the microfluidic unit 43, cultivation media, cryoprotective agents or water can be specifically introduced into the interior of the first chamber 20 and/or the second chamber 30, especially in an automated manner.

According to the invention it is not absolutely necessary for the microfluidic unit 43 to be firmly connected to the substrate device 100. Rather, the microfluidic unit 43 can be separate from the first and second chambers 20, 30, as shown in FIG. 9. In this case the microfluidic unit 43 preferably serves a dual function, in particular for delivery of the cultivation liquid and for delivery of the cooling medium. The microfluidic unit 43 can be provided in a fixed position, e.g. above the substrate device 100, for example as part of the cultivation device 200 according to FIG. 2, in order to introduce liquids into the first or second chamber 20, 30, respectively, which is located on the upper side of the substrate device 100 in the cultivation or temperature control state. The embodiment of the invention shown in FIG. 9 has the particular advantage that the steps of the delivery of at least one cultivation liquid 3.1, 3.2, the cooling medium and the heating medium are capable of being fully automated.

Alternatively, at least one microfluidic unit can be integrated into a cover and/or a wall of the first and/or second chamber. For example, another microfluidic unit can be provided for introducing the cooling medium, e.g. liquid nitrogen, into the second chamber.

FIGS. 9B to 9F schematically illustrate the course of the cryopreservation with the substrate device 100 and the microfluidic unit 43. According to FIG. 9B, when the substrate device is in the cultivation state, a first cultivation liquid 3.1 is directed into the first chamber 20 by the microfluidic unit 43. The substrate device is then rotated through 180° on the chamber holder 50 so that the first chamber 20 is facing downwards and the first cultivation liquid 3.1 flows out of the first chamber 20 (FIG. 9C). After a further rotation through 180°, when the first chamber 20 is again arranged on the upper side of the substrate device, another cultivation liquid 3.2 is filled into the first chamber 20 by the microfluidic unit 43 (FIG. 9D). The last step is the vitrification of the sample 1 according to FIG. 9E. This is done by rotating the substrate device 100 through 180° once again so that the second chamber 30 is arranged on the upper side of the substrate device. Cooling medium 5, e.g. liquid nitrogen, is filled into the second chamber 30 by the microfluidic unit 43.

Finally, FIG. 9F schematically illustrates the recovery of the sample 1, a heating medium 8, e.g. heated water, and washing substances for washing out cryoprotective agents being added to the first chamber 20 by the microfluidic unit 43.

Figure 10:
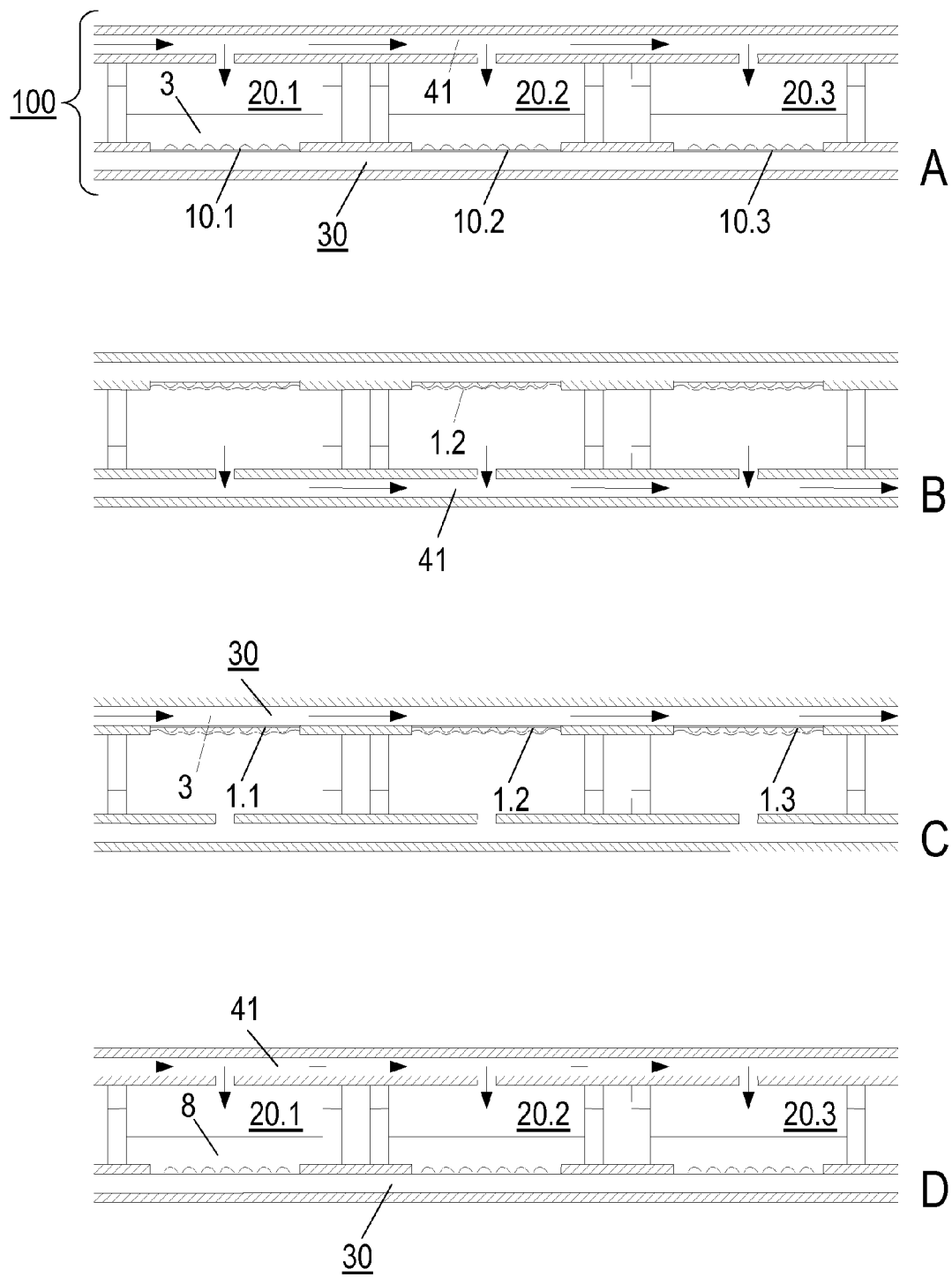
FIG. 10 (A-D) schematic sectional views of another embodiment of the substrate device according to the invention with a large number of sub-chambers.
Figure 11:
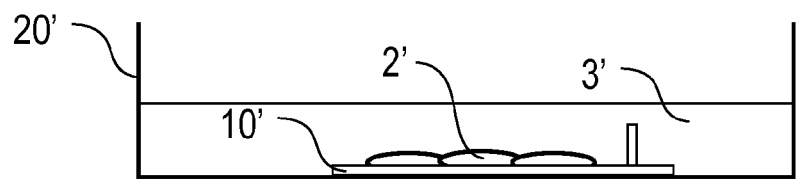
FIG. 11 (A-C) a schematic illustration of the conventional cryopreservation of adherent biological cells (prior art).
Figure 11:
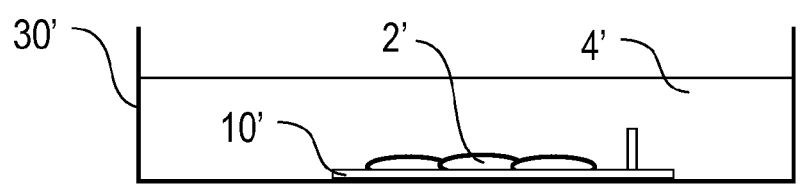
Figure 11:
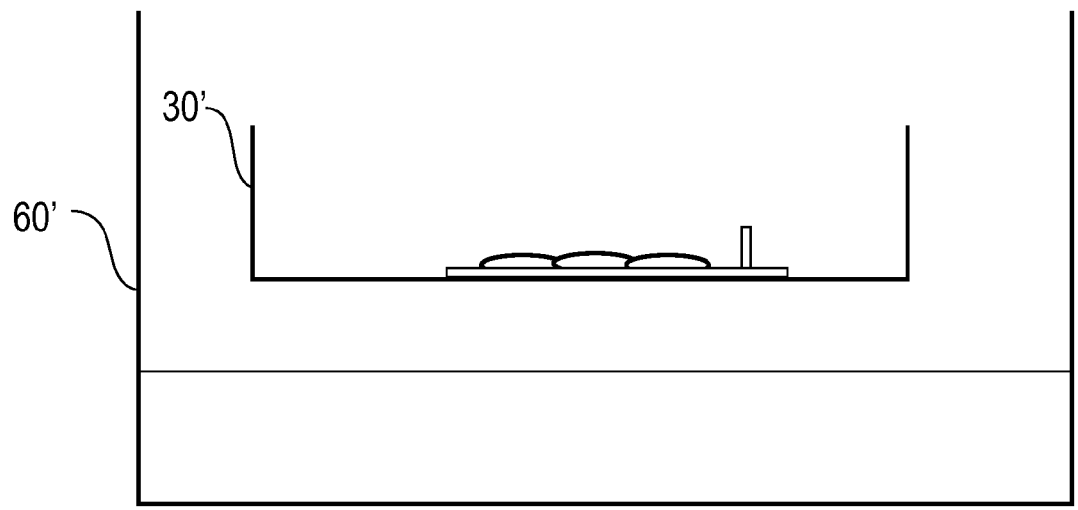

FIG. 10 illustrates another embodiment of the substrate device 100 according to the invention, where the first chamber comprises a large number of sub-chambers 20.1, 20.2, 20.3, . . . , which each have a substrate platform 10.1, 10.2, 10.3, . . . and are arranged adjacent to a second chamber 30. A first media line 41 is provided for directing a cultivation liquid 3 into the sub-chambers 20.1, 20.2, 20.3, ... (FIG. 10A) or withdrawing it from these sub-chambers (FIG. 10B). For the introduction and withdrawal of at least one cultivation liquid, the substrate device 100 can be rotated through 180° each time, as described with reference to the embodiments shown above. For the vitrification of the samples 1.1, 1.2, 1.3, . . . , a cooling medium 5, e.g. liquid nitrogen, is directed into the second chamber 30 via a second media line (FIG. 10C) when the substrate device 100 is in the temperature control state. FIG. 10E correspondingly illustrates the recovery of the samples, for which a heating medium 8 is directed into the sub-chambers 20.1, 20.2, 20.3, . . . via the first media line 41 in the cultivation state of the substrate device 100.

The embodiment of the substrate device 100 according to FIG. 10 advantageously forms a compact structure in which all the delivery and withdrawal lines are contained in the device and are matched to the properties of the substrate platforms. Advantageously, it is possible for media changes, media additions, incubation, vitrification and thawing to be fully automated and carried out with several samples simultaneously. This obviates the need for opening and for the manual withdrawal or addition of media or cryoprotective agents.

The features of the invention disclosed in the above description, the drawings and the claims can be significant, both individually and in combination, for realizing the invention in its various configurations.

The invention claimed is:

1. A substrate device for the cryopreservation of a biological sample including biological cells, comprising
   a substrate platform having a front side and a back side, the front side of the substrate platform forming a cultivation surface for receiving the biological sample, and
   a first chamber, in which the cultivation surface of the substrate platform is included, the first chamber being configured for receiving a cultivation liquid, wherein the first chamber is separated from surroundings by a cover,
   a second chamber, which is configured for receiving a temperature control medium, and
   a chamber holder, which is configured for receiving the substrate device in a cryopreservation apparatus in a pivotable manner, wherein the chamber holder comprises supporting elements being arranged in a plane parallel to an extent of the substrate platform and defining a lateral axis of rotation, which supporting elements can be pivotably coupled with an external support, wherein
   the first chamber and the second chamber are connected to each other in an adjacent manner,
   the substrate platform forms a separating wall between the first chamber and the second chamber, the back side of the substrate platform facing towards the second chamber and forming a liquid-tight closure with the second chamber, and
   the first chamber and the second chamber are configured such that the biological sample in the first chamber is isolated from the temperature control medium in the second chamber, so that there is no exchange of substances between the first chamber and the second chamber.

2. The substrate device according to claim 1, wherein
   the back side of the substrate platform is exposed in the second chamber, and
   the substrate platform is formed with a thickness and a thermal conductivity which, when the back side of the substrate platform is wetted with a first temperature control medium at a temperature below −120° C., allow vitrification of the biological sample on the cultivation surface.

3. The substrate device according to claim 1, wherein the substrate platform has at least one of the following features:
   the substrate platform has a thickness below 200 μm,
   the substrate platform is made of glass, plastic, semiconductor material or metal, and
   the substrate platform is made of a transparent material.

4. The substrate device according to claim 1, wherein the substrate platform is detachably connected to the first or second chamber via a liquid-tight substrate holder.

5. The substrate device according to claim 1, which has at least one of the following features:
   the substrate platform is connected to the first or second chamber via a compensating section, the compensating section being configured for absorbing temperature-dependent stresses between the substrate platform and the first or second chamber, and
   the first chamber has a pressure equalizing valve which is configured for equalizing the pressure between the first chamber and its surroundings.

6. The substrate device according to claim 1, wherein the substrate platform is an integral component of the first or second chamber.

7. The substrate device according to claim 1, which comprises
   a delivery device, which is configured for delivering at least one of the cultivation liquid and/or the temperature control medium.

8. The substrate device according to claim 7 wherein the delivery device comprises at least one of at least one media line and a microfluidic unit.

9. The substrate device according to claim 1, wherein the first and second chambers are detachably connected to each other.

10. The substrate device according to claim 9 wherein the second chamber is firmly connected to a chamber frame, which is configured for detachably receiving the first chamber.

11. The substrate device according to claim 9, wherein the first chamber is connected to the second chamber via a screw joint.

12. The substrate device according to claim 1, wherein the first chamber comprises several sub-chambers which are arranged adjacent to the second chamber, the substrate platform forming a separating wall between the sub-chambers and the second chamber.

13. The substrate device according to claim 2, wherein the backside of the substrate platform is wetted with liquid nitrogen.

14. A cryopreservation apparatus, comprising
   at least one substrate device according to claim 1, and
   a rotating device, which is configured for receiving the at least one substrate device, wherein
   the substrate device, by the rotating device being capable of pivoting between a cultivation state, in which the substrate platform forms the floor of the first chamber, and a temperature control state, in which the substrate platform forms the floor of the second chamber.

15. A method for the cryopreservation of a biological sample containing biological cells, using a substrate device according to claim 1, comprising the following steps:

providing the biological sample on the cultivation surface of the substrate platform in the first chamber, the biological cells being surrounded by a cultivation liquid, and receiving a cooling medium into the second chamber, which is adjacent to the first chamber and is connected to the latter in such a way that the substrate platform forms the separating wall between the first chamber and the second chamber, the temperature of the substrate platform being lowered and the biological sample being converted to a frozen state, wherein the cultivation of the biological cells comprises the following steps:

providing the first chamber and the second chamber in a cultivation state, in which the substrate platform forms the floor of the first chamber and the cultivation liquid is filled into the first chamber, and receiving the biological cells in the adherent state on the cultivation surface of the substrate platform, wherein the first chamber and the second chamber are pivoted into a temperature control state, in which the substrate platform forms the floor of the second chamber, and the cultivation liquid flows out of the first chamber, before the cooling medium is received in the second chamber.

16. The method according to claim 15 wherein the cultivation of the biological cells comprises the following steps:

providing the first chamber and the second chamber in a temperature control state, in which the substrate platform forms the floor of the second chamber, and receiving the biological cells in droplets of the cultivation liquid, which are suspended from the cultivation surface of the substrate platform.

17. The method according to claim 15, wherein the temperature of the substrate platform is lowered at a cooling rate such that the biological sample is vitrified.

18. The method according to claim 15, wherein the biological sample includes biological cells of different types, which are subjected to a common cultivation on the cultivation surface.

19. The method according to claim 15, comprising the following step:

receiving a heating medium into the second chamber, the temperature of the substrate platform being raised and the biological sample being converted to a thawed state.

* * * * *